United States Patent [19]
DeBaene et al.

[11] Patent Number: 6,108,819
[45] Date of Patent: Aug. 29, 2000

[54] PANTS WITH DETACHABLE BACK SUPPORT

[76] Inventors: David DeBaene, 60 Peters La.; Steev Panneton, 358 Washington St., both of West Warwick, R.I. 02891

[21] Appl. No.: 09/198,646

[22] Filed: Nov. 24, 1998

Related U.S. Application Data

[63] Continuation of application No. 09/103,894, Jun. 24, 1998.

[51] Int. Cl.⁷ .............................. A61F 5/02; A41D 1/06; A41D 13/02
[52] U.S. Cl. ........................................ 2/227; 2/237; 2/44
[58] Field of Search ................................. 2/44, 227, 231, 2/236, 237; 602/19

[56] References Cited

U.S. PATENT DOCUMENTS

| | | |
|---|---|---|
| 4,813,080 | 3/1989 | Toso . |
| 4,833,730 | 5/1989 | Nelson . |
| 5,038,408 | 8/1991 | Debaene . |
| 5,105,474 | 4/1992 | Skinner . |
| 5,157,790 | 10/1992 | Aldridge . |
| 5,398,667 | 3/1995 | Witt . |
| 5,402,539 | 4/1995 | Hewitt . |
| 5,450,627 | 9/1995 | Grilliot et al. . |
| 5,471,680 | 12/1995 | Vesterinen . |
| 5,634,215 | 6/1997 | DeBaene . |
| 5,819,320 | 10/1998 | Jolla . |

*Primary Examiner*—John J. Calvert
*Assistant Examiner*—Shirra L. Jenkins
*Attorney, Agent, or Firm*—Wolf, Greenfield & Sacks, P.C.

[57] ABSTRACT

Pants for use when performing work involving heavy lifting which providing removable back support to the wearer. The pants are constructed with an attachment apparatus, such as Velcro® brand hook and loop type fastener material, affixed to the waist area. A back support is also provided which has an attachment apparatus designed to fasten securely to the attachment apparatus of the pants. While attached to the pants the back support is comfortable and remains in a supportive position, yet may be easily removed when unnecessary or when cleaning the pants.

15 Claims, 3 Drawing Sheets

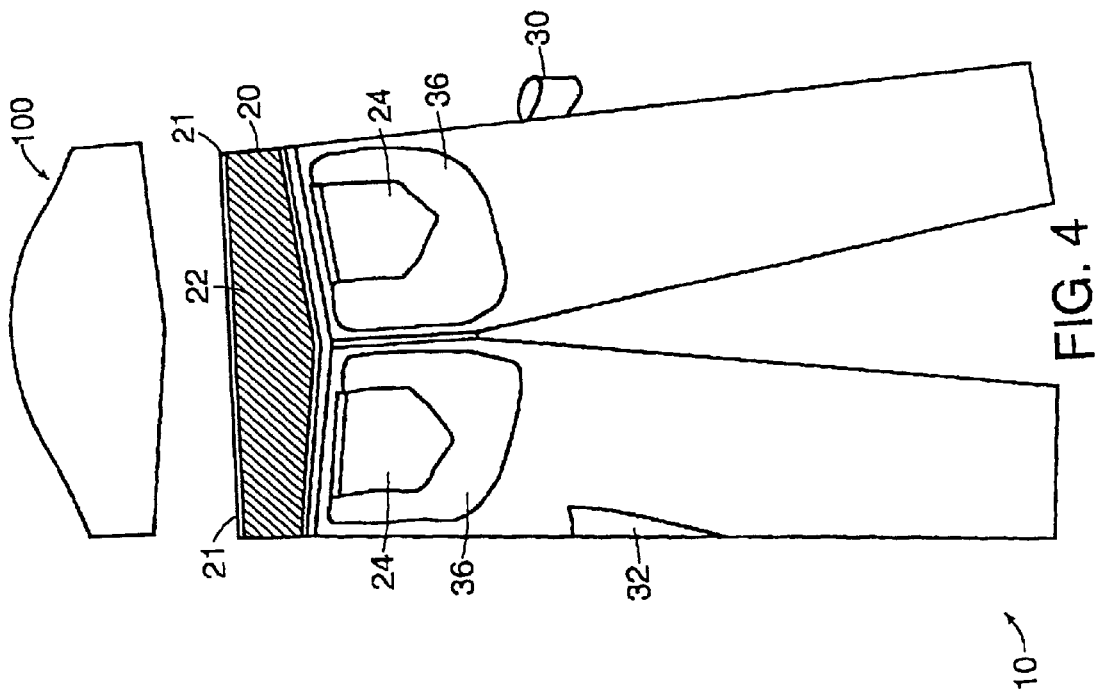
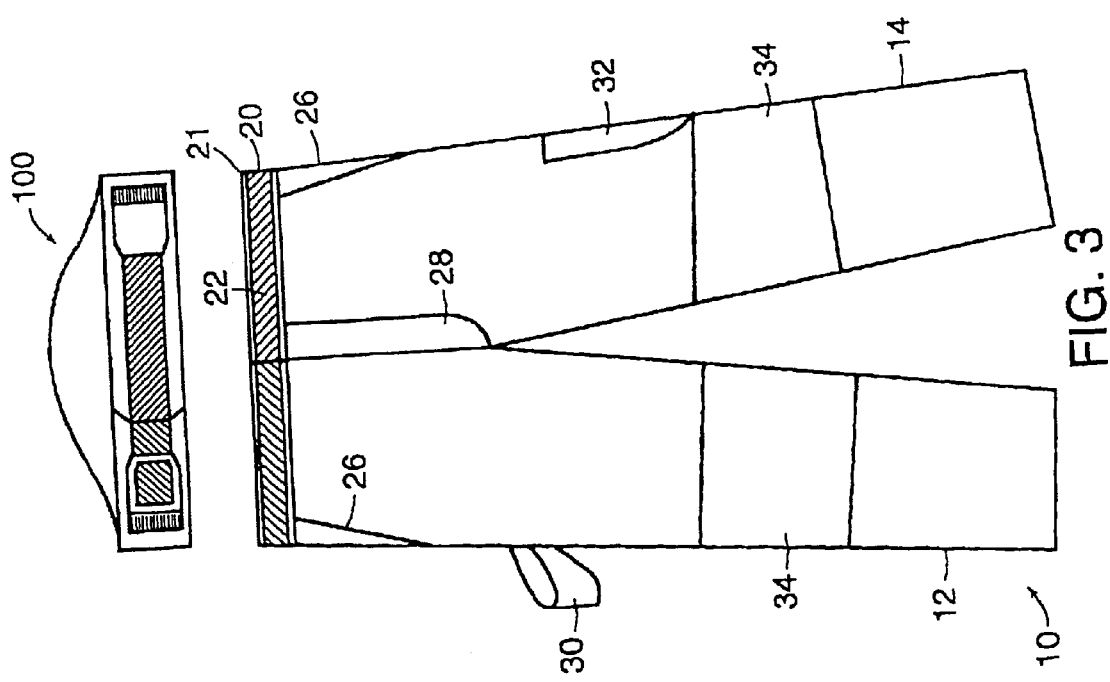

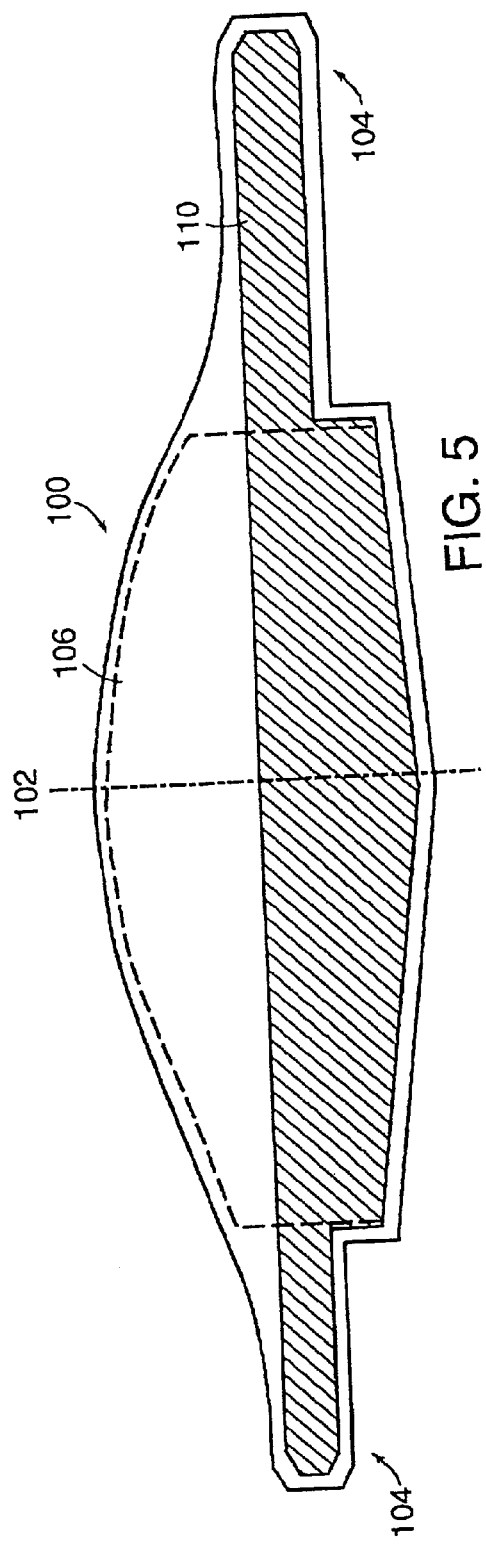
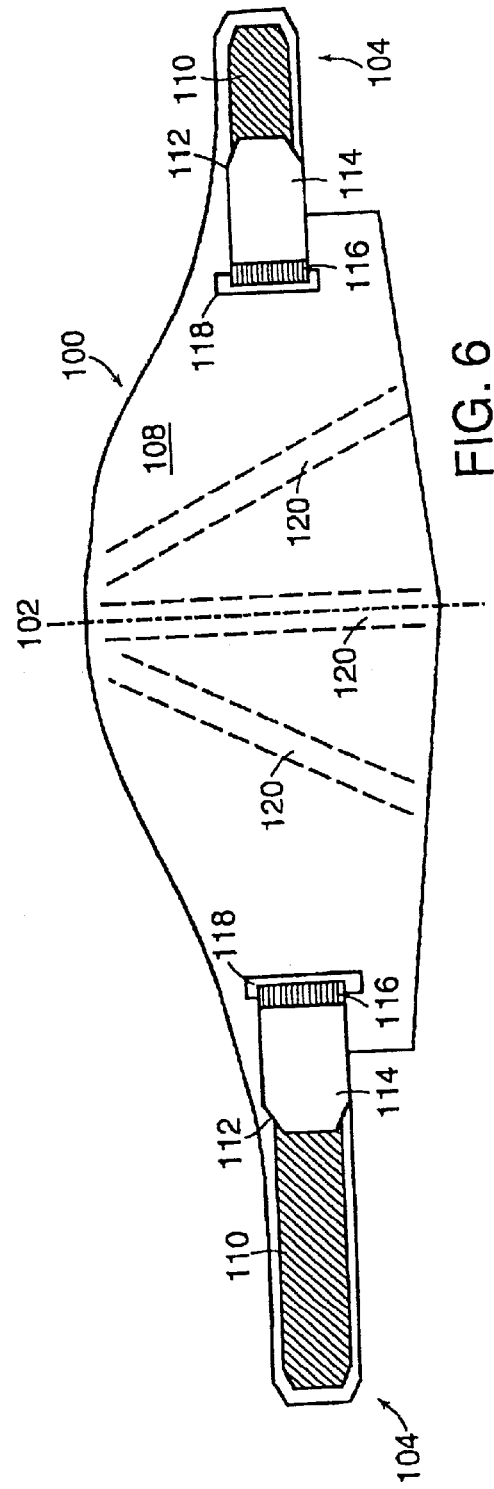

PANTS WITH DETACHABLE BACK SUPPORT

This application is a continuation of application Ser. No. 09/103,894, filed Jun. 24, 1998, entitled PANTS WITH DETACHABLE BACK SUPPORT, and now pending.

BACKGROUND AND SUMMARY OF THE INVENTION

This invention relates generally to clothing, and more particularly to a work pant garment which is designed to be worn by workers engaged in heavy lifting.

There are certain situations in the construction, shipping, and industrial trades in which a worker performs heavy lifting. An example of such a job is a stock person in a warehouse who moves heavy boxes. A worker who does heavy lifting experiences stress on his or her lower back which can lead to injuries. Typically, to help prevent such injuries a worker performing these jobs wears a back support consisting of a semi-rigid belt or strap that is wrapped around the worker's waist and cinched by a standard tightening mechanism. However, back supports are often uncomfortable and may be prone to shifting during use. As a consequence, supports may not be worn properly, or not worn at all, and thus may not provide adequate support. One solution to this problem is to fix the back support to the worker's pants. However, since the support is the most expensive part of the pants, and a worker needs many pairs of pants, using an integral back support can be very expensive.

The integral back support construction, while providing stable support for the back, suffers from several drawbacks. Since the support is the most expensive part of the pants, and a worker typically needs several pairs of pants, using an integral back support can be very expensive. Additionally, there is presently a need for a stable back support that can be removed when the worker is not doing lifting, and for cleaning.

The present invention is directed to a work pant garment for use by a wearer engaged in heavy lifting. The garment comprises an upper portion that and pant legs that are integrally joined to the upper portion and that extend downwardly therefrom, as well as a back support which is attachable to the waist portion of the pants, and an attachment mechanism for securing the attachment. Both of the upper and lower portions of the pants are formed of a woven material. The back support may be formed of any material which is stiff enough to give support, while pliable enough to be comfortable. The support may be attached to the pants with zippers, buttons, hook/loop type fasteners, snaps, hooks, equivalent devices, or any combination thereof.

Accordingly, among the several objects of the present invention are the provision of a work pant garment which supports the back of the wearer. Another object of the invention is to provide a stable back support which is easily removable. Still another object of the invention is to provide a work pant garment that is easily cleaned and inexpensive, yet has a back support. Yet another object of the invention is simple, rugged, and aesthetically pleasing work pant garment that will provide support for a wearer's back. One work pant that may be advantageously used with a detachable back support is shown in my U.S. Pat. No. 5,038,408, and another is shown in my U.S. Pat. No. 5,634,408, both of which are incorporated herein by reference.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention:

FIG. 3 is a front perspective view of a work pant garment and detachable back support of the present invention with the back support detached from the pant;

FIG. 4 is a rear perspective view thereof;

FIG. 5 is an interior view of the detached back support; and

FIG. 6 is an exterior view of the detached back support.

Corresponding reference numerals designate corresponding parts throughout the several views of the drawings.

DETAILED DESCRIPTION OF THE PREFERRED EMBODIMENT

Figure 2:
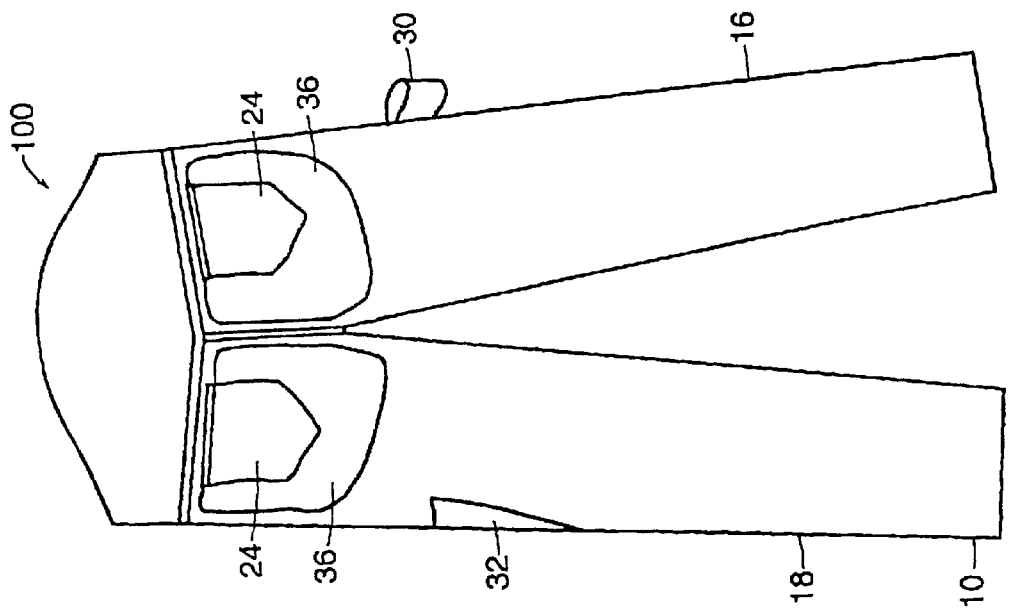
FIG. 2 is a rear perspective view thereof.
Figure 1:
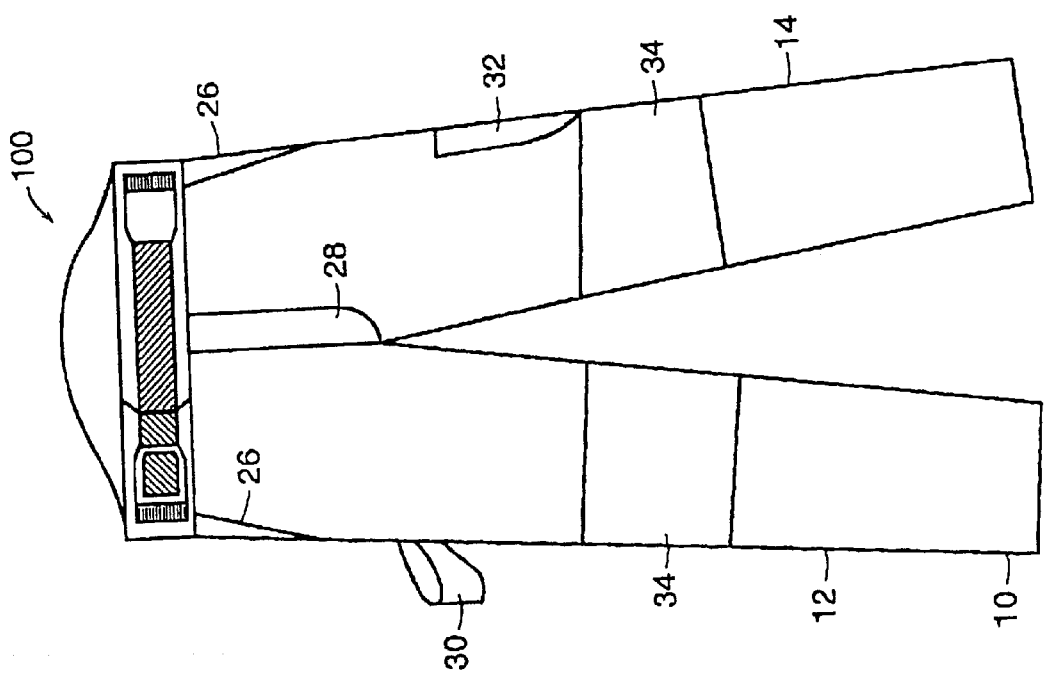
FIG. 1 is a front perspective view of a work pant garment and detachable back support of the present invention with the back support joined to the pant.

There are several preferred embodiments of this invention which vary with the application of the invention. For example, lightweight uniform pants with a detachable back support are preferred for a delivery person who sometimes handles heavy boxes, while heavy duty pants with reinforced knees and seat are preferred for construction workers. In some applications, overalls or a jump suit with a detachable back support are preferred.

Referring now to the drawings, and more particularly to FIGS. 1, 2, 3 and 4, there is generally indicated at 10 a work pant garment of the present invention with a detachable back support. The garment 10 is suited for use by a wearer who performs heavy lifting, such as in construction or shipping work, for example.

As illustrated in FIGS. 1, 2, 3, and 4, the arrangement of the garment 10 is of conventional design, the garment 10 having a front right leg panel 12 and front left leg panel 14 (seen FIG. 1 and 3), and a rear right leg panel 16 and a rear left leg panel 18 in the rear (seen FIG. 2 and 4). The garment also has an upper portion 20 which fits around the waist of the wearer (seen FIG. 3 and 4). The pant legs panels 12, 14 are integrally joined with pant leg panels 16 and 18 in the typical manner and the tops of the pant leg panels 12, 14, 16, 18 are integrally joined with the upper portion 20. The upper portion 20 is secured to one portion of a hook and loop type fastener material such as that provided by Velcro U.S.A., or other attaching means, such as a zipper or buttons 22. The upper edge of the upper portion 20 defines a waistband 21. The attaching means may include one or more hook and loop type fasteners, buttons or zippers.

The rear leg panels 16, 18 of the garment 10 optionally each have a pocket 24 sewn therein. The pocket 24 may be a patch pocket or any other style pocket as known in the art. The front leg panels 12, 14 of the garment 10 optionally each have a pocket 26 which is sewn therein. This pocket 26 also could be a patch pocket or any other style pocket as known in the art, and a fastening arrangement 28 sewn therebetween, including a zipper and a top button for securing the garment 10 to the wearer after it has been put on. Optionally, along opposite seams between the pant leg front and rear panels 12, 14, 16, 18 are a hammer or a utility loop 30 which is sewn to the right front pants panel 12 at its outer side and a pocket 32 which is sewn across the seam of the left front pants panel 14 and the left rear pants panel 16, the pocket 32 being suitably sized for holding pencils and other larger objects, such as utility knives.

The upper portion 20 and the pant leg panels 12, 14, 16, 18 of the garment 10 are formed of a woven material that is comprised of heavy duty yarns. More particularly, the portions 12, 18 are preferably fabricated from 8½ ounce blended twill fabric material which is taken from a blend of 65 percent polyester and 35 percent cotton. This fabric is of high quality and is particularly durable and rugged. However, it should be understood that the upper portion 20 and pant leg portions 12, 14, 16, 18 may be fabricated from any of a number of suitable fabric materials which are durable and comfortable to wear.

The back support 100 is shown both attached to the garment 10 (FIG. 1, 2) and detached from the garment 10 (FIG. 3, 4). A detail of the inside of one back support 100 adapted to be used in the present system is shown at FIG. 5, and a detail of the outside of that back support is shown at FIG. 6. The back support is widest at the center 102 where it will contact the wearer's back and narrowest at the ends 104 where it fastens in front of the wearer. The back support 100 is constructed from an inside layer of woven material 106 and an outside layer of woven material 108 sewn together at the edges. The lower interior of the back support 100, where it is to be engaged with the garment 10, has one or more pieces of hook and loop type fastener material 110 such as Velcro® brand faster material, or other attaching means such as zippers, buttons or hocks securely attached thereto. Also, the outer ends 104 of the back support 100 have a Velcro® brand hook and loop fastener or equivalent fastening means attached. The back support 100 can be constructed to securely hold the garment 10 at the proper height around the waist of the wearer without additional support such as a belt or suspenders.

Two slits 118 cut in the outside of the back support 100 allow an inner belt 112 to pass between the two layers of woven material constituting the back support 100. The inner belt 112 is constructed of two cloth panels 114 on either end, the outer of which can be seen in FIG. 6 and the inner of which are covered with hook and loop type fastening material, such as Velcro® brand fastening material such that they can engage with the fastening material on the back support ends 104. The panels 114 are sewn to an elastic band 116 which connects the two ends of the inner belt 112. One outside cloth panel 114 and one inside cloth panel 114 are covered with a hook and loop type fastening material such as Velcro® brand fastener so as to be easily and securely joined when the back support 100 is placed around the user's waist. In another embodiment of the invention, a buckle or other cinching mechanism is used to fasten the belt around the user's waist.

Between the inner belt 112 and the inside woven layer 106 of the back support 100 is a foam pad which covers substantially the entire inside of the back support 100. Three support members 120 constructed of a semi-rigid material such as a plastic are affixed to the foam pad by covering them with a woven layer and sewing them and the woven layer to the pad. The support member which is in the center 102 of the back support 100 is sewn to the inner layer 106, the outer layer 108, and the inner belt 112, fixing all these parts in relation to one another. It is to be understood that these layers need not be fixed together to within the scope of this invention.

Optionally, the back support 100, and garment 10 can be constructed such that the garment 10 will not remain around the worker's waist unless the back support 100 is properly engaged to the garment 10. This insures that the worker wears the back support 100 correctly, preventing potential injuries and bringing the worker in compliance with any company, industry or governmental safety policies.

The front leg panels 12, 14 of the garment 10 each have a overlay panel 13 affixed thereto by suitable stitching. As shown, the overlay panels 34 of the pant legs are located at the knee portions thereof. As illustrated in FIG. 2, 4, there are two overlay panels 36 located on the upper rear leg panels in the seat region; however, a single overlay panel covering the entire seat region may be provided and still fall within the scope and spirit of the present invention. Each overlay panel 34, 36 is preferably fabricated from an abrasion-resistant material that is defined by woven yarns that are selected from a group consisting of nylon and polypropylene. More particularly, the panels 34, 36 are formed of a blended weave of nylon and polypropylene materials which have an unusually high abrasion resistant quality. This blended weave can be purchased from commercial resources and is sometimes referred to as "NPMTBA Mill fabric No. 151,012,000". This product can be in the form of Kevlar® fabric material, Cordura, or ballistic cloth. This type of material has highly abrasive-resistant properties which possess superior strength and bursting strength characteristics, as well as superior tensile and tearing strength characteristics. It is to be understood that the overlay panels 34, 36 are only preferred for workers who will be experiencing extra wear on the knees and/or seat. Additionally for those workers who will be seated or kneeling frequently, it is preferred to supplement the overlay panels with padding materials.

The pant garment 10 of the present invention, after being assembled to assume its configuration illustrated in FIGS. 1 2, 3, and 4, can be treated with any number of chemicals, dyes and other materials for water proofing it and for obtaining a desirable color. The processing of the pant garment 10 can be conducted in accordance with well-known procedures in the art.

The operation and advantages of the present invention will now be readily understood in light of the above-description. It is clear that the pant garment 10 is particularly useful in construction, shipping and moving work.

When the work pant garment 10 of the present invention is used in construction and other similar work which causes stress on the lower back, the advantages over commercially available work pants and back supports are readily appreciable. The back support 100 is constructed to remain in place to give proper support while being easily removed for cleaning and when not required.

Many workers have their pants provided to them by a uniform supply business. Uniform supply businesses provide clothing to workers in a wide variety of industries from mechanics to warehouse crews. By using a uniform supply company, employers are assured that workers have a neat and consistent appearance to present to the public, and the team spirit and morale of workers are improved. Normally, clothing may be either rented or purchased from the uniform supply company. Though the exact procedure will vary with the uniform supply company and the needs of the industry being serviced, typically the company provides each worker with one pair of pants for each work day, and one day a week they pick up the worker's used pants and drop off cleaned pants. Additionally, the company will usually repair damaged pants and replace ones which are worn out. This means that for an industry with a 5 day work week, a worker must have at least 11 pairs of pants, 5 to wear during the week, 5 to be at the uniform supply company being cleaned and repaired, and one to wear the day the cleaner arrives. Thus the cost advantage of not having to provide a back support for each pair of pants is substantial.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. Apparel with removable back brace comprising:
   an article of apparel
   a first fastening apparatus affixed to the article of apparel;
   a back support structure, comprising:
      an outer wall,
      an inner wall affixed to the outer wall, defining a channel there between, and
      an inner belt passing through the channel and being covered by the channel for a majority of its length, and having a first and second end affixed to an elastic central portion; and
   a second fastening apparatus affixed to the back support structure;
   wherein the first fastening apparatus may be engaged with the second fastening apparatus to removably affix the back support structure to the article of apparel.

2. The apparel of claim 1, wherein the article of apparel consists of a pair of pants which have a reinforcing means constructed to protect a wearer's knees and add to the durability of the pair of pants.

3. The pair of pants of claim 2 further comprising a reinforcing means constructed to protect a wearer's seat and add to the durability of the pair of pants.

4. The apparel of claim 3, wherein the reinforcing means constructed to protect a wearer's knees and the reinforcing means constructed to protect a wear's seat comprise a padding means.

5. The apparel according to claim 4 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

6. The apparel according to claim 3 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

7. The apparel according to claim 2 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

8. The apparel of claim 1, wherein the article of apparel consists of a pair of pants which have a reinforcing means constructed to protect a wearer's seat and add to the durability of the pair of pants.

9. The apparel according to claim 8 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

10. The apparel of claim 1, wherein the article of apparel consists of a pair of uniform pants.

11. The apparel according to claim 10 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

12. The apparel of claim 1 wherein the back support structure fastens about the wearer with a cinching mechanism.

13. The apparel according to claim 12 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

14. The apparel according to claim 1 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

15. The apparel according to claim 14 wherein the first fastening apparatus and the second fastening apparatus comprise one or more fasteners chosen from the group consisting of: hook and loop type fasteners, zippers, snaps, buttons and buttonholes, hooks and eyes, and equivalent fasteners.

* * * * *